United States Patent [19]

Goledzinowski et al.

[11] Patent Number: 5,463,158
[45] Date of Patent: Oct. 31, 1995

[54] OLIGOMERIZATION OF LOW MOLECULAR WEIGHT OLEFINS IN AMBIENT TEMPERATURE MELTS

[75] Inventors: Maciej Goledzinowski, Gloucester; Viola I. Birss, Calgary, both of Canada

[73] Assignee: Her Majesty the Queen in right of Canada, as represented by the Minister of Energy, Mines and Resources, Ontario, Canada

[21] Appl. No.: 206,276

[22] Filed: Mar. 7, 1994

Related U.S. Application Data

[63] Continuation of Ser. No. 14,227, Feb. 5, 1993, abandoned, which is a continuation-in-part of Ser. No. 838,949, Feb. 21, 1992, abandoned.

[51] Int. Cl.$^6$ ..................................................... C07C 2/14
[52] U.S. Cl. ........................... 585/520; 585/526; 585/527
[58] Field of Search ................................ 585/532, 526, 585/527, 520, 514, 515; 502/224

[56] References Cited

U.S. PATENT DOCUMENTS

| | | | |
|---|---|---|---|
| 3,842,134 | 10/1974 | Pratt | 585/255 |
| 4,198,534 | 4/1980 | Mandai et al. | 585/16 |
| 4,912,195 | 3/1990 | Jansons et al. | 528/222 |
| 5,012,030 | 4/1991 | Lane et al. | 585/527 |

OTHER PUBLICATIONS

Catalysis Today, Apr. 10, 1992, pp. 1, 8, 9, 42, 43, 73 and 74, Elsevier Science Publishers, Amsterdam.

*Primary Examiner*—P. Achutamurthy
*Attorney, Agent, or Firm*—Fish & Richardson

[57] ABSTRACT

An improved process is described for the catalytic oligomerization of light olefins, such as ethylene or propylene. Higher hydrocarbons, such as gasoline grade hydrocarbons, are produced from the light olefins using a liquid catalyst which comprises a Lewis acid and a Lewis base component which forms with the Lewis acid a melt which is liquid at room temperature. The Lewis acid is a metal halide, such as aluminum trichloride and the Lewis base is an organic salt, such as an organic halide salt containing an N-heterocyclic ring or salts containing fully substituted onium ions.

4 Claims, No Drawings

OLIGOMERIZATION OF LOW MOLECULAR WEIGHT OLEFINS IN AMBIENT TEMPERATURE MELTS

CROSS-REFERENCE TO RELATED APPLICATION

This application is a continuation of Ser. No. 08/014,227, filed Feb. 5, 1993, now abandoned, which is a continuation-in-part of Ser. No. 07/838,949, filed Feb. 21, 1992, now abandoned.

BACKGROUND OF THE INVENTION

This invention relates to an improved process for the catalytic oligomerization of light olefins to higher hydrocarbons and particularly to a novel oligomerization catalyst used in the process.

DESCRIPTION OF THE PRIOR ART

Recently, light hydrocarbons have become increasingly attractive feedstocks for petrochemical and fuel application. Considerable effort has been placed on the development of light hydrocarbon and refinery by-product recovery and processing to high-quality gasoline and chemicals. The optimum use of light products is even more critical in view of the progressive decrease in the use of lead compounds in fuels.

The use of heterogeneous catalysts for dimerization and oligomerization of olefins has been known for some time. Nickel oxide supported on silica or silica-alumina and various nickel salts (nitrate, chloride, sulphate) deposited on silica, alumina and silica-alumina have all been successfully used as catalysts. Recently, nickel-exchanged zeolites have been employed for the oligomerization of alkenes. The process conditions, conversions and selectivities to higher hydrocarbons depend on the nature of nickel catalysts. For example, Chauvin et al., Appl. Catal., 42 (1988) 205 obtained 97% conversion of propylene with 66% dimerization selectivity at 40° C. and a pressure of 4 bar on $NiSO_4$ supported on alumina as the catalyst. Elev et al., J. Catal. 89 (1984) 470 obtained a 15–20% conversion during ethylene dimerization with a selectivity of 62% to butene at room temperature and a pressure of 9.3 kPa on the NiCaY zeolite catalyst which was reduced by a photo-assisted means. Nickel-exchanged NaY zeolite has also been used for the oligomerization of ethylene into a diesel-range product at a pressure of 3500 kPa and a temperature of 100° C.–300° C.

Oligomerization of alkenes is catalyzed by strong acids. A commercial catalyst for the oligomerization of alkenes contains concentrated (90%) orthophosphoric acid in a mixture with Kiselguhr and is called "silicophosphoric acid". Ethylene and propylene oligomerize over this catalyst at +300° C. and at an initial pressure of 5.1–6.1 kPa giving alkanes, alkenes, cycloalkanes and aromatic hydrocarbons. Ethylene also oligomerizes and polymerizes in the presence of $AlCl_3$ and HCl as co-catalyst at super atmospheric pressure, producing liquid paraffin hydrocarbons and addition compounds of $AlCl_3$ with highly unsaturated cyclic compounds corresponding to the formula $C_nH_{2n-x}AlCl_3$.

Zeolites from the pentasil family have been successfully used for oligomerization of olefins. Mobil's olefin to gasoline (MOGD) process serves as a good example. This process has two major concerns: controlling the heat of reaction and maximizing the yield of either gasoline- or distillate-range products.

A recent process, Alphabutol, involving the dimerization of ethylene to butene-1 is described in Commereuc et al., Hydrocarbon Processing, November 1984, p. 118. The Alphabutol process uses a homogeneous catalyst. Ethylene is converted at 50°–60° C. and low pressure in the liquid phase which contains a titanium-based catalyst. Butene-1 is produced as the main product (65 wt %) along with higher molecular weight by-products (pentene, hexene).

Jansons et al. U.S. Pat. No. 4,879,366, issued Nov. 7, 1989 describes the production of aromatic oligomers by reacting an appropriate monomer system in the presence of a co-catalyst in the form of a complex between a Lewis acid and a Lewis base. The Lewis acid is typically aluminum trichloride, while the Lewis base may include a wide range of organic halide salts.

Lane et al. U.S. Pat. No. 5,012,030, issued Apr. 30, 1991, describes a process for producing isobutylene polymers utilizing a co-catalyst comprising aluminum trichloride and an organic nitro compound.

Pratt, U.S. Pat. No. 3,842,134 issued Oct. 15, 1974 relates to the polymerization of olefins using a catalyst comprising a mixture of anhydrous aluminum chloride and a mononitroalkane, e.g. mononitromethane.

Mandai et al, U.S. Pat. No. 4,198,534, issued Apr. 15, 1980 describes subjecting olefins to cationic polymerization using Lewis acid catalyst or Lewis acid/Lewis base complex catalyst.

It is the object of the present invention to provide a process for converting low molecular weight hydrocarbons into gasoline grade higher hydrocarbons.

SUMMARY OF THE INVENTION

In accordance with the present invention, it has been discovered that higher hydrocarbons, and particularly gasoline grade hydrocarbons, can be efficiently produced from low molecular weight olefins by using as catalyst a molten salt mixture which is liquid at ambient temperatures. The molten salt mixture is typically a mixture of a Lewis acid, e.g. an inorganic halide such as aluminum trichloride and a Lewis base component, e.g. an organic halide salt capable of forming with the Lewis acid a melt which is liquid at room temperature. It has been found that high yields of the higher hydrocarbons are obtained and the ratios of the individual higher hydrocarbons can be varied depending upon the composition of the melt being used as catalyst.

Room temperature melts or molten salt systems are known in the literature and are described for instance in Jones et al., J. Electrochem. Soc., Vol. 136, No. 2 (1989) 424. These melts have been primarily of interest as electrolytes for battery applications. The room temperature melts are typically prepared by combining inorganic salts, such as aluminum chloride, and certain organic salts, such as the alkylpyridinium chlorides. The molten salt mixture is prepared by simply combining the two solids. In some cases, some external heat may be needed but usually the melt begins to form spontaneously upon mixing the two solids.

When used as a catalyst according to the present invention, the Lewis acid portion of the melt can be any of the well-known Lewis acids. A Lewis acid is a substance which can accept an unshared electron pair from another molecule and may include aluminum trichloride, aluminum tribromide, antimony pentachloride, indium trichloride, gallium trichloride, boron trichloride, zinc chloride, ferric chloride, stannic chloride, titanium tetrachloride, etc. However, an aluminum halide, such as aluminum trichloride is preferred.

The Lewis base portion is a substance capable of donating an unshared electron pair to a Lewis acid an can be selected from a wide range of organic salts capable of forming a room temperature melt with the Lewis acid portion. However, particularly preferred as the Lewis base portion are organic halide salts containing an N-heterocyclic ring and organic salts containing fully substituted onium ions. The central atom of the onium ion can be nitrogen, phosphorus (quaternary ammonium or phosphonium) or sulphur (ternary sulphonium). Preferably, at least one of the substituents should be an aromatic radical such as phenyl or benzyl. The other substituents are preferably small aliphatic groups such as methyl or ethyl. The side chain can contain ethereal oxygen. For use as an oligomerization catalyst, the Lewis acid and Lewis base portions are preferably in the molar ratio of about 1:2 to 2:1.

The low molecular weight feedstocks are typically light ends from petroleum processing containing 2 to 4 carbon atoms, e.g. low molecular weight olefins such as ethylene and propylene. The oligomerization is carried out by passing these low molecular weight olefins through the liquid catalyst at a temperature between 0° C. and 150° C. and a pressure between 10 kPa and 1,000 kPa.

The products obtained are typically mixtures of $C_4$–$C_6$ hydrocarbons. Not only are these products obtained in good yield but it has been surprisingly discovered that the ratios of the different $C_4$–$C_6$ hydrocarbons may be varied by varying the composition of the liquid catalyst. For instance, when using as catalyst a melt of $AlCl_3$ and N-n-butylpyridinium chloride, overall ethylene conversion to $C_4$–$C_6$ hydrocarbons was as high as 80%, with selectivity for $C_4$ compounds of about 86%.

There is a fundamental difference between the catalysts used in the process of this invention and the catalysts used in the prior patents of Jansons et al, Lane et al, Pratt and Mandai et al mentioned above. This fundamental difference exists even though components forming the catalysts of the prior patents may individually be similar to the components of the catalysts used in the present invention.

Pratt and Lane et al. dissolve $AlCl_3$ Lewis acid in basic, organic solvent, e.g. nitromethane in order to improve the yield of oligomers. The real catalyst is $AlCl_3$ whereas nitromethane acts only as a solvent and controlling agent. Nitroparaffin in Lane et al. allows solubilization and fluidization of the $AlCl_3$ catalyst which is not able to act as oligomerization catalyst while insoluble in the reaction mixture. Jansons et al. claim the action of Lewis acid/Lewis base complex as a solvent for the polymer/Lewis acid complex formed during reaction. Thus, the inventions of the prior art improve only the acid-catalyzed oligomerization of alkenes which basically takes place without basic co-catalyst according to the well known mechanism called cationic polymerization, as shown below:

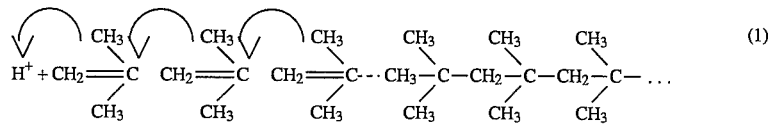
(1)

where $H^+$ ions are produced as a result of $AlCl_3$ hydrolysis in the presence of small amount of water:

 (2)

The dissolution of $AlCl_3$ catalyst in organic, basic solvent (e.g. nitromethane) may lead to the situation where $AlCl_3$ itself or $AlCl_3$-base complex acts as an electron acceptor in the oligomerization process.

In this well known, classic approach, the only active catalyst is $AlCl_3$ (or $H^+$ ions resulting from $AlCl_3$ hydrolysis) and the presence of organic base (e.g. nitromethane) is not required for the oligomerization process to proceed. The acid induced oligomerization proceeds very well without Lewis base, as shown by Pratt's Examples 1 and 2. The dissolution of the active catalyst, $AlCl_3$, in a basic organic solvent (e.g. nitromethane) improves only the yield of oligomerization product. It is common knowledge that acidic salt ($AlCl_3$) dissolves in basic solvent. Of course, as the result of this dissolution the acid-base complex may be formed of the formula:

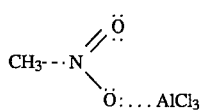

which is being dissolved in the excess of nitroalkane. The role of organic, basic solvent is limited here to keep the $AlCl_3$ catalyst as a fluid, as pointed out by Lane et al. The basic character of this solvent is obvious as the $AlCl_3$ catalyst is a strong Lewis acid.

The above shown $AlCl_3$-Lewis base complex represents a donor-acceptor character of bonding between an electron acceptor ($AlCl_3$) and an electron donor (Lewis base, e.g. nitromethane). In these classes of compounds the chemical bond between two components is well defined and localized strictly between donor and acceptor atoms. Therefore, these compounds may be usually separated as a crystalline phase which is also well known in the prior art.

In the case of molten salt catalyst of this invention, Lewis acid ($AlCl_3$) is not dissolved in the Lewis base and no acid-base complex is formed. As the result of mixing of $AlCl_3$ (Lewis acid) with organic salt (RCl, Lewis base) as shown herein, a pure mixture of ions (not acid-base complex) is formed, according to the reactions:

 (3)

 (4)

where $R^+$ denotes an organic cation, e.g. imidazolium, N-n-butylpyridinium. In order to produce a melt under ambient conditions, as described herein, the molar ratio of $AlCl_3$ and RCl is maintained approximately within the range of about 1:2 to 2:1, which is a simple consequence of the above equilibrium reactions (3) and (4). Reaction (4) is completely analogous to the Bronsted acid-base properties of water ($2H_2O = H_3O^+ + OH^-$) where a Lewis acid ($AlCl_3$) transfer occurs between two amphoteric anions. The ionic composition of the melt is dependent only on $AlCl_3$/RCl ratio (within the range of about 1:2 to 2:1). There is no complex formed between Lewis acid and Lewis base and also no solution of Lewis acid in Lewis base is produced by mixing of $AlCl_3$ with RCl. Instead, due to a spontaneous reaction between $AlCl_3$ and RCl a mixture of ionic species, according to equilibrium reactions (3) and (4), is formed. The specific conductivities of these melts are comparable with conductivities of diluted aqueous solutions of inorganic salts. These conductivities are much higher than those of $AlCl_3$-organic base complexes in organic solvent.

One of the main reasons contributing to the low melting temperature behaviours of $AlCl_3/RCl$ mixtures is the delocalization of the interaction between acid and base due to large size of pi electron cloud in aromatic organic salt. The delocalization of interaction means that the entropy of the melt is considerably enhanced over separate $AlCl_3$ and RCl solids so that a lower melting temperature will result. In fact, X-ray crystallographic studies have shown that at least the acidic melts (with $AlCl_3/RCl$ ratio>1) are unlikely to possess any degree of ordering in the liquid phase that arise from a very weak (if any) hydrogen bond to chloroaluminate anions. This supports the fact that the formation of Lewis acid/Lewis base complex is not possible in the case of molten salt systems. If the interaction between Lewis acid and Lewis base were more localized as with an unshared pair of electrons or an unfilled orbital, a strong interaction may occur and crystalline adduct formation rather than low melting behaviour will result. Such adducts, with strongly localized acid-base interaction are formed when $AlCl_3$ is dissolved in basic electrolytes, e.g. nitromethane, as described in the prior patents. This kind of crystalline adducts between inorganic salt and organic solvent is well known in the scientific literature.

The simple structural considerations, as presented above, show the principal difference between molten salt catalytic system of this invention and Lewis acid-Lewis base complex of the prior art. As pointed out above the active catalyst in the prior patents is $AlCl_3$ or $AlCl_3$-basic solvent complex. In the case of $AlCl_3/RCl$ melts the catalytic system is composed of mixture of $Al_2Cl_7^-$; $AlCl_4^-$; $Cl^-$ and $R^+$ ions. The only entity which may be considered as an acceptor of olefinic electron (and the acting catalyst) is organic cation, $R^+$. Therefore the mechanism of olefin oligomerization in the presence of ambient temperature melts is clearly different from that catalyzed by $AlCl_3$ or $AlCl_3$-organic solvent complex.

This difference in the mechanism of olefin oligomerization according to this invention also has important advantages as stated above. Thus, not only are mixtures of $C_4$–$C_6$ hydrocarbons obtained in good yields, but with the molten salt catalyst of this invention it has very surprisingly been discovered that the ratios of the different $C_4$–$C_6$ hydrocarbons in the product may be varied by varying the composition of the catalyst.

DESCRIPTION OF THE PREFERRED EMBODIMENTS

The following examples illustrate the process and compositions of the instant invention but are not to be construed as limiting the scope of the invention.

Example 1

A melt catalyst was prepared by combining together aluminum trichloride and pyridinium hydrochloride in the molar ratio 2:1. The two solids readily formed into a room temperature melt. This melt catalyst was used for the oligomerization of ethylene and propylene by passing the ethylene or propylene through the melt. The identification of the hydrocarbon products was confirmed by gas chromatographic (GC) and mass spectroscopic (GC/MS) methods.

(a) Using ~160 g of the melt at 80° C. and an ethylene flow rate of 20 mL/min, the overall conversion reached 90% during the first 19 hours of operation. Thereafter, the conversion decreased almost linearly and then reached ~15% after 32 hours of operation. An average selectivity to $C_2$–$C_6$ fraction was ~36%. The selectivity of each hydrocarbon product within this fraction changed with time, but was relatively stable during the first 20 hours of operation. The selectivities are shown in Table 1 below:

TABLE 1

| Hydrocarbon | Selectivities (%) at time of operation | |
| --- | --- | --- |
|  | 10 h | 32 h |
| ethane | 2.5 | 0.05 |
| $C_3$ (propane) | 7.5 | 0.1 |
| $C_4$ unsaturated | 30.0 | 19.5 |
| $C_4$ saturated | 40.0 | 27.0 |
| $C_5$ unsaturated | 14.0 | 24.0 |
| $C_6$ unsaturated | 5.5 | 29.0 |

Also, a small amount of methane (maximum selectively 0.01%) was monitored during the first few hours of operation.

(b) When propylene was passed through the melt (~160 g) at 80° C. and a flow ratio of 20 mL/min, the overall conversion reached 100% during the first 28 hours of operation. Thereafter, the conversion decreased and reaches ~10% after 51 hours. An average selectively to $C_1$–$C_6$ fraction was ~65%. The selectivity to each hydrocarbon product within this fraction was relatively stable during the first 28 hours and then changes as shown in Table 2 below:

TABLE 2

| Hydrocarbon | Selectivities (%) at time of operation | |
| --- | --- | --- |
|  | 10 h | 51 h |
| $C_3$ (propane) | 8.5 | 0.0 |
| $C_4$ unsaturated | 60.0 | 29.5 |
| $C_4$ saturated | 11.0 | 3.0 |
| $C_5$ unsaturated | 18.5 | 37.0 |
| $C_6$ unsaturated | 1.5 | 30.5 |

Also, a small amount of methane and ethane (maximum selectivity 0.004 and 0.13%, respectively) was monitored, although methane appeared only during the first hours of operation.

The solids products, which accumulated in the melt, were analyzed by GG/MS method. The results showed a mixture of high molecular weight compounds (MW<262) containing saturated and unsaturated hydrocarbons and/or chlorinated unsaturated hydrocarbons. The difference between each mass fragment was typically 14 corresponding to $CH_2$ fragments.

Example 2

A melt catalyst was prepared in the same manner as described in Example 1 using aluminum trichloride and N-n-butylpyridinium chloride in the molar ratio 2:1. Ethylene and propylene were again passed through melt at oligomerization conditions.

Using ~120 g of the melt at 40° C. and an ethylene flow rate of 20 mL/min, the overall conversion at the beginning of the process was ~80%, and achieved a steady-state value of ~30% after 5 hours which was maintained for the next 5 hours. An average selectivity to $C_1$–$C_6$ fraction was 100%. The steady-state selectivities to each hydrocarbon product were as follows: saturated $C_4$–74%, unsaturated $C_4$–12%, saturated $C_5$–7.5%, unsaturated $C_6$–6%, unsaturated $C_5$–0.1%, propane 0.05%, ethane—0.01%. The overall steady-state conversion decreased to 42% when a higher flow rate of ethylene (40 mL/min) was utilized at 40° C., while the selectivities remained practically unchanged.

(b) When propylene was passed through the melt (~100 g) at 80° C. and a flow rate of 20 mL/min, the overall conversion was 100% during the first 8 hours, then decreased almost linearly and reached ~20% after 28 hours. An average selectivity to $C_1$–$C_6$ fraction was ~35%. The selectivity to each hydrocarbon product changed with time, but eventually achieved the values in Table 3 below:

TABLE 3

| Hydrocarbon | Selectivities (%) at time of operation | |
|---|---|---|
| | 9 h | 28 h |
| $C_3$ (propane) | 7.0 | 0.0 |
| $C_4$ unsaturated | 52.5 | 22.0 |
| $C_4$ saturated | 7.0 | 0.1 |
| $C_5$ unsaturated | 0.0 | 13.0 |
| $C_5$ saturated | 29.0 | 30.5 |
| $C_6$ unsaturated | 4.5 | 34.0 |

Also, small amounts of methane and ethylene (maximum selectivity 0.002 to 0.09% respectively) were monitored during the first four hours of operation. At lower temperature, e.g., 40° C., both the overall conversion and the selectivities were lower, although this effect was rather minor.

The liquid products, which accumulated in the melt, were analyzed by GC/MS methods. The results showed that a mixture of high molecular weight compounds (MW<206) containing saturated and unsaturated hydrocarbons were produced. The difference between each mass fragment was typically 14.

Example 3

Once again using the same procedure as in Example 1, a melt catalyst was prepared by combining aluminum trichloride and 1-methyl-(3-ethyl)-imidazolium chloride in the molar ratio 3:2. Ethylene and propylene were separately passed through the melt at oligomerization conditions.

(a) Using ~120 g of the melt at 80° C. and ethylene flow rate of 20 mL/min, the overall conversion reached 70% during the first 4 hours of operation. Thereafter, the conversion decreased and then reached ~25% after 10 hours of operation. An average selectivity to $C_1$–$C_6$ fraction was 100%. The selectivity to each hydrocarbon product changed with time. These values were as shown in Table 4 below:

TABLE 4

| Hydrocarbon | Selectivities (%) at time of operation | |
|---|---|---|
| | 2 h | 10 h |
| ethane | 0.10 | 0.03 |
| $C_3$ (propane) | 0.4 | 0.01 |
| $C_4$ unsaturated | 18.0 | 18.0 |
| $C_4$ saturated | 72.0 | 36.5 |

TABLE 4-continued

| Hydrocarbon | Selectivities (%) at time of operation | |
|---|---|---|
| | 2 h | 10 h |
| $C_5$ unsaturated | 7.0 | 16.5 |
| $C_6$ unsaturated | 2.5 | 28.5 |

(b) When propylene was passed through the melt (~120 g) at 60° C. and 20 mL/min, the overall conversion reached 100% during the first 11 hours. Thereafter, the conversion decreased to ~50% after 31 hours. An average selectivity to $C_1$–$C_6$ fraction was 44%. The selectivity to each hydrocarbon product changed gradually with time. These values are shown in Table 5 below:

TABLE 5

| Hydrocarbon | Selectivities (%) at time of operation | |
|---|---|---|
| | 10 h | 31 h |
| ethane | 0.05 | 0.35 |
| $C_3$ (propane) | 9.0 | 13.0 |
| $C_4$ unsaturated | 67.0 | 53.0 |
| $C_4$ saturated | 5.0 | 2.0 |
| $C_5$ unsaturated | 17.5 | 27.5 |
| $C_5$ saturated | 0.1 | 0.35 |
| $C_6$ unsaturated | 1.0 | 3.5 |

Also, a small amount of methane (maximum selectivity 0.001%) was monitored at all times.

The liquid products, which accumulated in the melt, were analyzed by GC/MS methods. The results showed that a mixture of high molecular weight compounds (MW<183) containing saturated and unsaturated hydrocarbons were produced. The difference between each mass fragment was typically 14.

We claim:

1. A process for catalytic oligomerization of low molecular weight $C_2$–$C_4$ olefins to form higher hydrocarbons which comprises reacting said olefins under oligomerization conditions, in the presence of a catalyst consisting essentially of a molten salt mixture which is liquid at room temperature and is essentially free from organic solvent, said molten salt catalyst being obtained by combining (a) an aluminum halide in solid form and (b) a Lewis base component in solid form comprising an organic salt selected from the group consisting of organic halide salts containing a N-heterocyclic ring and organic salts containing fully substituted onium ions, in the molar ratio of aluminum halide: Lewis base of about 1:2 to 2:1, said molten mixture being a pure mixture of ions containing no aluminum halide dissolved in the Lewis base and containing no aluminum halide-Lewis base complex.

2. A process according to claim 1 wherein the aluminum halide is aluminum trichloride.

3. A process according to claim 2 wherein the oligomerization reaction is carried out at a temperature in the range of 0° C. to 150° C. and a pressure between 10 kPa and 1,000 kPa.

4. A process according to claim 3 wherein the higher hydrocarbon products obtained are $C_4$–$C_6$ olefins.

* * * * *

UNITED STATES PATENT AND TRADEMARK OFFICE
CERTIFICATE OF CORRECTION

PATENT NO. : 5,463,158
DATED : October 31, 1995
INVENTOR(S) : Maciej GOLEDZINOWSKI et al.

It is certified that error appears in the above-indentified patent and that said Letters Patent is hereby corrected as shown below:

On the title page, item [75], insert --Jan Galuszka, Nepean-- and change "both" to --all--.

Signed and Sealed this

Fifteenth Day of April, 1997

Attest:

BRUCE LEHMAN

*Attesting Officer*   *Commissioner of Patents and Trademarks*